United States Patent
McNeil

(10) Patent No.: US 7,985,590 B2
(45) Date of Patent: Jul. 26, 2011

(54) METHOD AND SYSTEM FOR DETECTION USING NANODOT TAGGANTS

(75) Inventor: Scott Earl McNeil, Ashburn, VA (US)

(73) Assignee: Science Application International Corporation, San Diego, CA (US)

( * ) Notice: Subject to any disclaimer, the term of this patent is extended or adjusted under 35 U.S.C. 154(b) by 0 days.

(21) Appl. No.: 12/855,853

(22) Filed: Aug. 13, 2010

(65) Prior Publication Data

US 2010/0304491 A1    Dec. 2, 2010

Related U.S. Application Data

(60) Continuation of application No. 11/404,829, filed on Apr. 17, 2006, now abandoned, which is a division of application No. 10/255,054, filed on Sep. 26, 2002.

(51) Int. Cl.
*G01N 23/00* (2006.01)
(52) U.S. Cl. .......................................................... 436/58
(58) Field of Classification Search ..................... 436/58
See application file for complete search history.

(56) References Cited

U.S. PATENT DOCUMENTS

| | | | |
|---|---|---|---|
| 3,772,099 A | 11/1973 | Ryan et al. ................. 149/18 |
| 4,363,965 A | 12/1982 | Soberman et al. ............ 250/302 |
| 5,196,396 A | 3/1993 | Lieber ................................ 505/1 |
| 5,252,835 A | 10/1993 | Lieber et al. ............... 250/492.1 |
| 5,262,357 A | 11/1993 | Alivisatos et al. ............ 437/233 |
| 5,505,928 A | 4/1996 | Alivisatos et al. ............ 423/299 |
| 5,537,000 A | 7/1996 | Alivisatos et al. ............ 313/506 |
| 5,614,435 A | 3/1997 | Petroff et al. ................. 437/110 |
| 5,710,005 A | 1/1998 | Rittenburg ......................... 435/6 |
| 5,751,018 A | 5/1998 | Alivisatos et al. .............. 257/64 |
| 5,776,713 A | 7/1998 | Garner et al. ................ 435/7.92 |
| 5,840,435 A | 11/1998 | Lieber et al. .................. 428/698 |
| 5,897,945 A | 4/1999 | Lieber et al. .................. 428/323 |
| 5,942,444 A | 8/1999 | Rittenburg .................... 436/518 |
| 5,990,479 A | 11/1999 | Weiss et al. ................... 250/307 |
| 5,997,832 A | 12/1999 | Lieber et al. .................. 423/249 |
| 6,025,200 A | 2/2000 | Kaish et al. ..................... 436/56 |
| 6,036,774 A | 3/2000 | Lieber et al. .................. 117/105 |
| 6,066,295 A * | 5/2000 | Bernstein et al. ............... 422/50 |
| 6,068,981 A | 5/2000 | Rittenburg .................... 435/7.1 |
| 6,140,134 A | 10/2000 | Rittenburg .................... 436/514 |
| 6,159,742 A | 12/2000 | Lieber et al. .................. 436/164 |
| 6,190,634 B1 | 2/2001 | Lieber et al. .................. 423/439 |
| 6,207,392 B1 | 3/2001 | Weiss et al. .................... 435/7.1 |
| 6,225,198 B1 | 5/2001 | Alivisatos et al. ............ 438/497 |
| 6,296,189 B1 | 10/2001 | Lawandy et al. ............. 235/491 |

(Continued)

OTHER PUBLICATIONS

Nanosys, "Developing Nano" [online], [retrieved on Oct. 16, 2003], 12 pp., Retrieved from the Internet: http://www.nanosysinc.com/technology.html.

(Continued)

*Primary Examiner* — Lore Jarrett
(74) *Attorney, Agent, or Firm* — King & Splading LLP

(57) ABSTRACT

Described herein are methods directed to the use of the nanodot taggants in detection and/or simulation scenarios. The nanodot taggants are based on quantum dots and may be engineered so as to have particular emission and or absorbance spectral characteristics. The nanodots are extremely small, i.e., on the order of nanometers in size, and thus do not, in some cases, behave as particles, but rather are able to be carried along and through structures like a gas.

3 Claims, 1 Drawing Sheet

U.S. PATENT DOCUMENTS

| | | |
|---|---|---|
| 6,303,516 B1 | 10/2001 | Morita et al. .................. 438/758 |
| 6,306,610 B1 | 10/2001 | Bawendi et al. ............... 435/7.1 |
| 6,306,736 B1 | 10/2001 | Alivisatos et al. ............. 438/497 |
| 6,343,063 B1 | 1/2002 | Rollhaus ....................... 369/286 |
| 6,370,316 B1 | 4/2002 | Yamada et al. ................. 386/46 |
| 6,379,622 B1 | 4/2002 | Polak et al. ................ 422/82.06 |
| 7,038,766 B2 | 5/2006 | Kerns et al. ..................... 356/71 |
| 2002/0008148 A1 | 1/2002 | Empedocles et al. ......... 235/494 |

OTHER PUBLICATIONS

Cigarette Tax Stamping System, [online], FUSON, [retrieved Sep. 17, 2002], 1 p, Retrieved from Internet: www.meyercord.com/fusonsys.html.

Electrochemical process makes ultra-small silicon nanoparticles, [online], News Bureau, [retrieved Sep. 17, 2002], 2 pp., Retrieved from Internet: www.news.uiuc.edu/scitips/00/03nanotip.html.

Brand Protection Specialists De La Rue and Microtag Join Forces with Launch of Revolutionary Anti-Counterfeiting Solution, Aug. 18, 1999, [online], DeLaRue, [retrieved on Sep. 17, 2002], 3 pp., Retrieved from Internet: www.delarue.com/news/articles/152.asp.

Microscopic and extremely durable— The SECUTAG®—Security-Code: Product Security, Product Authentication, Coded Identification—SECUTAG® is your reliable "fingerprint" on your products—Anti-counterfeit, [online], SECUTAG®, 2 pp., [retrieved on Sep. 17, 2002], Retrieved from Internet: www.secutag.com/security-code.html.

SECUTAG® is the state-of-the-art in color-coded micro-particles with layers >1µ. Our manufacturing technology and screening process make it unique within competing products, Anti-conterfeit, Anti-trademark piracy, Document security, [online], SECUTAG®, 2 pp., [retrieved on Sep. 17, 2002] Retrieved from Internet: www.secutag.com/identification-code.html.

Prepared by Betsy Schwartz, "Research Results", "*SAIC Knowledge Center (SKC), Corporate Development*", Sep. 12, 2002, 22 pp.

"Developing Nano", [online], Nanosys, [retrieved Jun. 20, 2002], 2pp, Retrieved from Internet: http://www.nanosysinc.com/technology.html.

Zhiyong Tang, Nicholas A. Kotov, Michael Giersig, "Spontaneous Organization of Single CdTe Nanoparticles into Luminescent Nanowires," *Science*, Jul. 12, 2002, p. 237-240.

Pike, John, "General Purpose Bombs," GlobalSecurity.org, 1 p., Feb. 20, 2002.

Yi Cui, Qingqiao Wei, Hongkun Park, Charles M. Lieber, "Nanowire Nanosensors for Highly Sensitive and Selective Detection of Biological and Chemical Species," *Science*, Aug. 17, 2001, p. 1289-1292.

Eric W. Wong, Paul E. Sheehan, Charles M. Lieber, "Nanobeam Mechanics. Elasticity, Strength, and Toughness of Nanorods and Nanotubes," *Science*, Sep. 26, 1997, p. 1971-1975.

"LazerTAGit™", Instant Brand AUTHENTICATION and PROTECTION!, 1 p., Meyercord Revenue.

J. Miragliotta, R. Osiander, "Use of Scatterer Controlled Emission for Optical Sensor Platforms, *The Applied Physics Laboratory*", pp. 19-15 to 19-24.

\* cited by examiner

METHOD AND SYSTEM FOR DETECTION USING NANODOT TAGGANTS

CROSS-REFERENCE TO RELATED APPLICATIONS

This application is a continuation application of and claims priority to U.S. patent application Ser. No. 11/404,829 entitled "METHOD AND SYSTEM FOR DETECTION USING NANODOT TAGGANTS," filed Apr. 17, 2006 now abandoned, which is a divisional of U.S. patent application Ser. No. 10/255,054 entitled, "METHOD AND SYSTEM FOR DETECTION USING NANODOT TAGGANTS," filed Sep. 26, 2002, both of which are incorporated herein by reference in their entirety.

BACKGROUND OF THE INVENTION

1. Field of the Invention

The present invention is related generally to the field of optical detection, and more particularly, to the field of optical detection and identification of additive taggants.

2. Description of the Related Art

Existing taggants are used by both private companies and individuals and the government in order to identify and authenticate numerous articles, such as financial documents (e.g., checks, stamps, vouchers, stock certificates, bonds, currency, passports, and the like). Further, attempts have been made by the government to use existing taggants to identify and track munitions, (e.g., bombs, and to perform bomb damage assessment ("BDA"). Although the identification of bombs prior to detonation is preferable, it is also important to detect and track the plume of a bomb, especially one containing biological warfare agents. Current taggants for BDA are made from rare-earth or organic materials. Unfortunately, it is necessary to add significant quantities to the explosive mixture of the bomb in order to be detected with stand-off sensors and the current taggants are prone to degradation during the explosion. Further, the existing taggants also have indiscriminate absorption spectra and are often difficult to detect above a background of spectral noise.

Taggants have also been used to test the safety and track the location of munitions, such as sporting firearms, ammunitions, and smokeless propellant powders. The types of taggants used are microscopic and sometimes magnetic particles that are mixed with explosives, and remain behind after the explosion, e.g., the firearm is discharged, takes place. Although invisible to the naked eye, under magnification these types of taggants are actually color coded pieces of a polymer material, e.g., plastic, that are meant to identify a particular batch of explosive powder. By tagging munitions when they are manufactured, it is possible to identify and return to this source in cases where the munitions were used in an illegal capacity, e.g., acts of terrorism, etc. Unfortunately, some studies have shown that the taggants used had an adverse effect on the propellant and explosive materials used in the munitions, thus causing the effectiveness and accuracy of the munitions to be reduced. This is due in some cases to the large quantities of taggant materials that were necessary in order to be detected post-discharge and other cases because of chemical interactions between the materials.

Prior art taggants have also been used in scenarios where it is necessary to differentiate between a friend or a foe in military or police situations. Referred to as "identification friend or foe" or IFF, this process uses an encrypted signal sent via radio frequency (RF) in order to identify friendly assets and resources and reduce fratricide. The signal is sent by an 'interrogator' and the reply is sent by a 'transponder'. These coded signals are changed at a given interval and require extensive supporting hardware.

Additionally, attempts have been made to use taggants in various other identification and/or detection scenarios, such as for identifying counterfeit or pirated goods. In addition to frequently pirated goods such as software, currency and credit cards, compact discs and videotapes, clothing, and aircraft parts, goods such as food products, beverages, pharmaceuticals, perfumes, and the like are also affected. And this list is not exhaustive. Nearly all consumer brand products, specialty chemicals, currency, or industrial products are susceptible to counterfeiting or tampering. In fact, according to the ICC Counterfeiting Intelligence Bureau, counterfeit products account for 5% of world trade, representing about US$250 billion annually. Taggants are useful as product markers to confirm authenticity.

Available technology for product identification includes, for example, bar codes, which are large, susceptible to wear and tear, require line-of sight reading, and usually identify categories of products as opposed to acting as unique identifiers. Another technology, Radio-frequency identification tags (RFIDs), do offer unique identifiers (unlike barcode tags), but as yet are no smaller than 1 mm by 0.5 mm and contain multiple breakable parts, such as a microchip and an antenna. This size is prohibitive for many applications. Further, the RF bands are subject to cross-talk and other interference and are not conducive to detection from too great a distance.

Still another taggant technology includes printing fluorescent marks on an item, such as a heat-sealable label, to generate a unique identification number or indicia. The unique identification number or indicia is then read by a reader system that includes an illumination source that excites the fluorescent marks in combination with a color sensitive device, such as a camera, which is "blind" to the illumination wavelength but which can discern the fluorescence color and a relative spatial order of the fluorescent marks. Such labels are limited in their application and are susceptible to wear and tear. Such labels cannot be used for BDA or other harsh environmental or long-range detection applications.

Yet another marking technology includes melamine alkyd polymer particles, which range in sizes from approximately 5-45 μm. The material is layered in various thicknesses to ascertain a code by way of 4 to 10 layers of variable coloration. The codes are read using a microscope with approximately 40 times magnification or automatic reading devices. This microscopic layering technology is susceptible to degradation and due to size limitations and reading requirements, is not suitable for many taggant situations described herein.

Finally, biological taggants have been used which are based on bio-engineered, recognition molecules used to detect and measure safe, inert markers, which have been added to products as an internal "fingerprint". In order to test for the presence of the taggant, it is necessary to either physically access the product for a real-time dipstick test or to conduct quantitative field and laboratory tests. These taggants are limited to use with certain petroleum, chemicals, pesticides, printing, food and beverages and require invasive testing to determine the presence thereof.

SUMMARY OF THE INVENTION

Summary of the Problem

The existing BDA taggants are in two broad categories. The rare earth taggants are made of a rare earth element such as scandium where, scandium does not degrade in an explosive environment. Explosive temperatures reach in excess of 1000 degrees Celsius and high pressures up into the hundreds, perhaps even thousands of psi, pounds per square inch. Rare earth taggants require a large amount of mass in order to be detected by a standoff sensor. Further, the emission and/or absorbance frequency or wavelength of the rare earth taggants is set. The current taggants cannot be engineered to emit at a different wavelength. Consequently, if the predetermined emission and/or absorbance frequency/wavelength is close to that of the surrounding environment, the taggants may be extremely difficult, if not impossible to detect.

A second category of BDA taggants is based on organic molecules such as organic dyes and fluorescent pigments. These carbon-based taggants do give off a robust signature and thus are easier to detect at a distance, but they frequently do not survive in a hostile release environment, e.g., an explosive environment. Carbon-based taggants degrade very rapidly when they see temperatures in excess of 120 Celsius. As such, there are many applications wherein carbon-based taggants would be useless due to the temperature considerations. Further, as with the rare earth taggants, carbon-based taggants do not have tunable wavelengths. Carbon-based taggants absorb at a broad wavelength, giving off at a broad frequency such that the signal to noise has not been optimized for these taggants.

There is a need in the art to conduct effective bomb damage assessment ("BDA"). When, for example, a war fighter strikes a facility with ammunition, whether that's a missile or bomb, there is a need to know the effect or damage caused. While there are visible means available to asses structural damage, there is little way of knowing the extent of the damage inside that facility. Further, there is a need in the art to track and/or simulate the plume of a target in the case where biological and chemical warfare agents as well as toxic industrial chemicals are released. There presently exists a need in the art for compounds that simulate or mimic the spectral signatures of agents of chemical and biological warfare (CBW). Due to their severe toxicity, these 'live' CBW agents must be handled with extreme caution and can not be dispersed into the environment. It is therefore very difficult to validate instruments that detect these CBW agents.

As described above, the taggants used in munitions identification pose degradation threats to the propellant and explosive materials and may cause long-term environmental damage.

Further, there is a need in the art for a robust, covert taggant that is easily detectable for use in the identification of a friend or foe in certain military or law enforcement situations.

Still further, there is a need in the art for a robust, covert taggant that is easily detectable for the identification, authentication, and policing of counterfeit products and the like.

Summary of the Solution

The present invention is directed to the use of the nanodot taggants in detection scenarios. The nanodot taggants are based on quantum dots. The nanodots are extremely small, i.e., on the order of nanometers in size, and thus do not, in some cases, behave as particles, but rather are able to be carried along and through structures like a gas. In an embodiment of the present invention, the nanodot taggant is added to an explosive material or in the proximity of an explosive material. When the explosive material reacts, the nanodots are distributed at a concentration that is high enough to be detected by a stand-off detector such as an infrared detector or multi-spectral detector. Further, the nanodots are formed of compounds that are more robust in high temperature and high pressure ranges and than organic or rare earth taggants and consequently are less susceptible to damage or destruction by the reaction. Using the stand-off detector data, the nanodots reveal, among other things, (a) that the explosive material actually reacted versus being a dud, (b) the approximate depth and location of the explosion, and (c) the track of the explosive material, e.g., the track of the plume of the explosive material or residue that is released. Further, the nanodot taggants are engineered to emit and absorb at very specific frequencies. Consequently, nanodot taggants are engineered, if necessary, to maximize detection according to the environment wherein the explosive material is expected to react. For example, if the explosive material is expected to react in a vegetative environment, with a predominately green background, it would be difficult to detect a taggant that is green against that background. Through nanodot taggant engineering, a non-green emission and/or absorbance wavelength, e.g., red, is selected in order to increase the signal to noise ratio.

In a further embodiment of the present invention, the nanodot taggant is used as an identification device. For example, in times of conflict, nanodot taggants can be used to identify target objects, e.g., tanks, as friends or foes. In this further embodiment, the target objects are marked with the nanodot taggant. This marking could be in the form of paint or some other mechanically visible marker, such as changeable panels or drainable panels that contain nanodot taggant-infused liquid. Stand-off detectors/transmitters are used to transmit a radiation band or bands for absorption by the nanodot taggants and detection of the emitted down-converted radiation band, i.e., frequencies, that identifies the target object as a friend or foe. Further to this embodiment, the markers containing the nanodot taggant or the nanodot taggants within the markers may be changed at predetermined intervals in order to avoid duplication by enemy objects attempting to deter or duplicate identification of friendly objects.

In still a further embodiment of the present invention, nanodot taggants are used to simulate the characteristics of biological and/or chemical agents. Through such simulations, diagnostic configurations, e.g., detectors and the like, may be optimized without the risk of exposure.

More particularly, a first embodiment of the present invention is directed to a system for detecting the characteristics of an explosive reaction. The system includes a component containing an explosive material and a nanocomponent taggant material, wherein at least a portion of the nanocomponent taggant material is released from the component upon reaction of the explosive material and further wherein the at least a portion of the nanocomponent taggant material emits at least one predefined radiation frequency; and a detector located within detection proximity of the reaction of the explosive material, wherein the detector detects the at least-one predefined radiation frequency.

A second embodiment of the present invention is directed to a method for detecting characteristics of an explosive reaction. The method includes transmitting at least a first radiation frequency in the direction of an explosive reaction, wherein the explosive reaction contains nanocomponent taggant material; and detecting at least a second radiation frequency, wherein the at least a second radiation frequency is emitted by at least a portion of the nanocomponent taggant material in response to the absorption of the at least a first radiation frequency.

A third embodiment of the present invention is directed to a method for detecting characteristics of an explosive reaction. The method includes determining the approximate spectral characteristics of an environment wherein an explosive reaction will be facilitated; engineering a nanocomponent taggant material to emit at least a first spectral frequency in order to account for the approximate spectral characteristics of the environment; adding the nanocomponent taggant material to a component, wherein the component causes the explosive reaction; facilitating the explosive reaction with the component in the environment; and detecting the at least a first radiation frequency, wherein the at least a first radiation frequency is emitted by at least a portion of the nanocomponent taggant material in response to the explosive reaction.

A fourth embodiment of the present invention is directed to a method for identifying at least one target object. The method includes marking the at least one target object with a nanocomponent taggant emitting at a first spectral frequency for a first specified time interval; transmitting a first absorption band towards the at least one target object during the first specified time interval and detecting the first spectral frequency from the at least one target object; removing the nanocomponent taggant emitting at the first spectral frequency and-marking the at least one target object with a nanocomponent taggant emitting at a second spectral frequency for a second specified time interval; and transmitting a second absorption band towards the at least one target object during the second specified time interval and detecting the second spectral frequency from the at least one target object.

A fifth embodiment of the present invention is directed to a method for tracking the path of a pollutant. The method includes engineering a nanocomponent taggant, wherein the nanocomponent taggant has the traveling characteristics of the pollutant and further wherein the nanocomponent taggant emits at least one predefined spectral frequency; adding the engineered nanocomponent taggant to the pollutant; and detecting the at least one predefined spectral frequency of the nanocomponent taggant, so as to track the path of the pollutant.

A sixth embodiment of the present invention is directed to a method for optimizing a detector for detecting a hazardous compound. The method comprises determining the spectral characteristics of the hazardous compound; engineering a set of nanocomponents, wherein the set of nanocomponents simulates the spectral characteristics of the hazardous compound; detecting the set of nanocomponents; and optimizing the detector for detecting the hazardous compound based on the detection of the set of nanocomponents.

A seventh embodiment of the present invention is directed to a method for authenticating at least one product. This method includes adding a predetermined number of nanocomponents to the at least one product, wherein the nanocomponents have a known spectral absorbance characteristic and a known spectral emission characteristic; directing radiation having the known spectral absorbance characteristic in the direction of the at least one product, wherein the predetermined number of nanocomponents emit the known spectral emission characteristic in response to absorption of the known spectral absorbance characteristic; and detecting the known spectral emission characteristic, wherein detection of the known spectral emission characteristic authenticates the at least one product.

BRIEF DESCRIPTION OF THE FIGURES

In the figures.

DETAILED DESCRIPTION OF THE PREFERRED EMBODIMENTS OF THE PRESENT INVENTION

Figure 1:
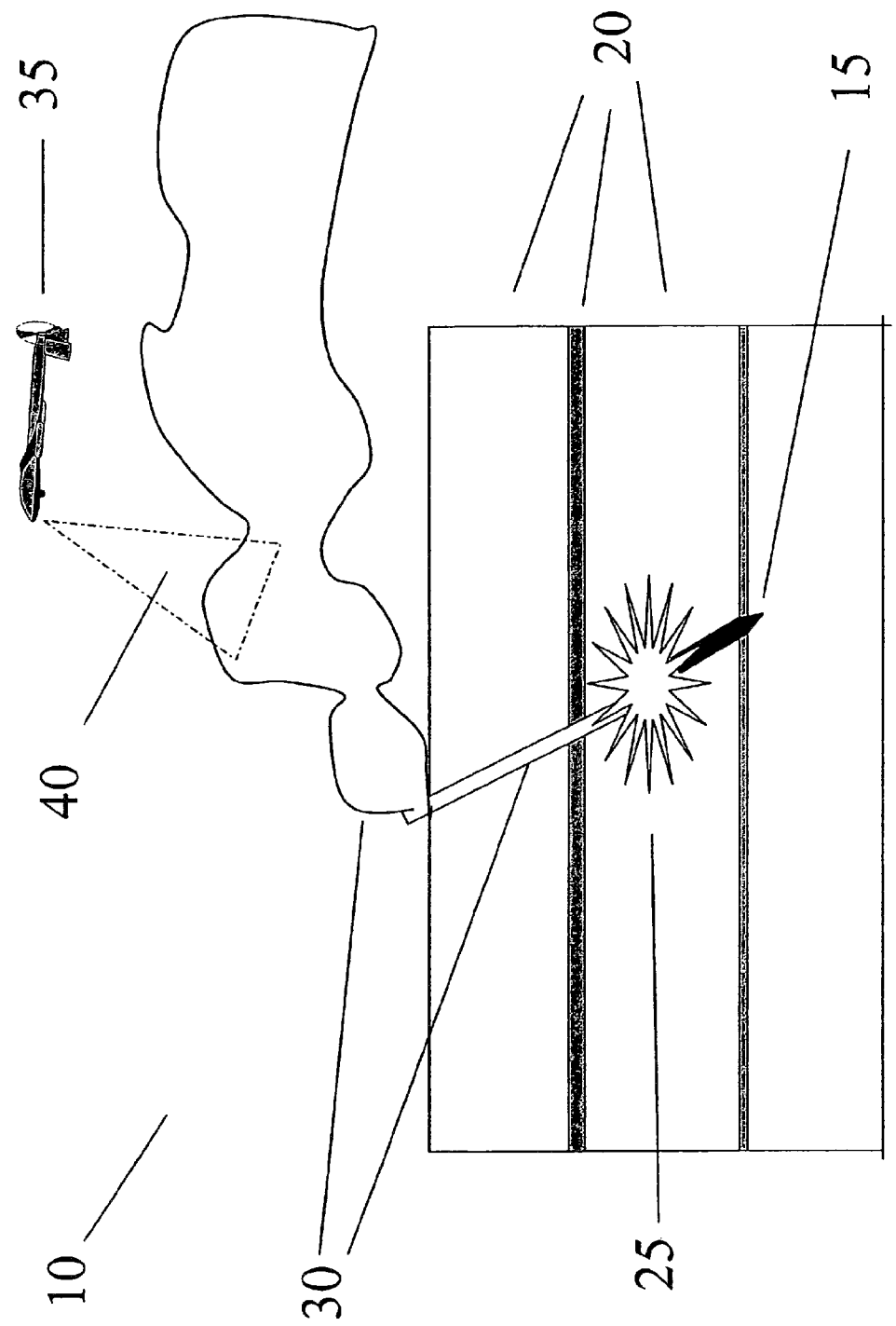
FIG. 1 depicts a system for detecting nanodots according to an embodiment of the present invention.

Referring to FIG. 1, a system 10 for detecting nanodot taggants according to a first embodiment of the present invention is shown. In FIG. 1, an explosive device 15 detonates after traveling through multiple layers 20 of structural material (e.g., earth, building, etc.). The resulting plume or residue 30 is released from the point of detonation 25 and eventually travels away from the multiple layers of structural material 20. According to an embodiment of this invention, the plume contains nanodot taggants that were released, like the plume, from the explosive device upon detonation. Further, the nanodot taggants are engineered so as to emit at a predetermined frequency or frequencies in response to detonation of the explosive device. This emission may be triggered by the sun, i.e., ultraviolet radiation, a thermal activator, i.e., the explosion itself, or the absorption of a certain frequency or frequencies of radiation transmitted by a predetermined source. As such, upon detonation, the nanodot taggants within the plume emit at the predetermined frequency or frequency range of radiation that is detectable by the stand off detector 35. The process whereby the nanodot taggants absorb radiation and in response emit radiation is referred to as down-converting.

Alternatively, the stand-off detector 35 or a separate transmitter (not shown) also operates in a transmission mode, wherein the stand-off detector 35 transmits a predetermined frequency of radiation or range of radiation frequencies 40 towards the multiple layers of structural material. The nanodot taggants within the plume absorb at some or all of the radiation frequencies 40 transmitted by the stand-off transmitter/detector 35, causing the nanodot taggants to emit a frequency or frequency range of radiation that is detectable by the stand off detector 35.

The concept of down-converting is based on what presently occurs with organic dyes. A particular dye will absorb at one frequency, for example, the fluorescent dyes will absorb in the ultraviolet such as at 300 nanometers, and the dye will emit radiation at a higher wavelength, with a lower energy. So the concept of down converting is where high energy, low wavelength radiation is absorbed and higher wavelength, lower energy radiation is emitted. Organic dyes absorb and emit at very broad wavelengths. The emission and/or absorbance wavelength ranges between various dyes bleed over into each other. Consequently, if multiple dyes are used, there is cross-sensitivity and cross-emission and/or absorbance between the dyes. Nanodots are entirely different. Nanodots absorb at a given wavelength or given series of wavelengths and they emit at very sharp wavelengths that are narrow in width. For example, a nanodot that emits at 300 nanometers, can absorb at anything below 500 nanometers but emits a narrow spike on a spectral band centered at 500 nanometers, not a broadband distribution band as one would see with an organic or fluorescent dye. Nanodots can be engineered to absorb and emit at any of an almost infinite number of unique spectrums. Nanodots are capable of emitting at a unique spectral signature. For example, multiple nanodots with multiple wavelengths of emission and/or absorbance, can be mixed together, and are entirely compatible with each other. The emitted spectral signatures can be engineered so as not to bleed together and are separately detectable. A single transmission at, for example, 300 nm, could result in one, dozens, or even thousands of unique emitted spectral spikes depending on the nanodot characteristics.

Nanodots are also referred to as quantum dots and as nanocrystals. Although described throughout as "nanodots,"

the characteristics and uses described herein of nanodots extend to other nanocomponents such as nanorods, nanowires, and nanotubes. Throughout the description herein, they will be referred to as nanodots. A nanodot generally has dimensions in the nanometer range, e.g., up to 100 nm. The nanodot taggants described herein are capable of withstanding temperatures in excess of 1,000 degrees Celsius and several hundred psi of pressure for a duration of at least one second. The nanodot taggants are uniquely designed and engineered for a number of frequencies. Nanodot taggants can be engineered in the ultraviolet, visible, and IR spectrums, covering a range of thousands of nanometers. For example, nanodots made out of InAs can be engineered to absorb and emit in a range of 700 to 2,000 nanometers, from the visible to the IR. In engineering the characteristics of the nanodots, the diameter of the nanodot is directly related to the absorption and emission characteristics of the nanodot. Another example is a CdSe nanodot that can be engineered to absorb light in the visible blue region anywhere from 400 into the 600 nanometers. Further, InP can be engineered to create nanodots that absorb and emit in the visible green region, from 500 into the 700 nanometer range. These are but a few examples of the materials and frequency ranges from and for which nanodots can engineered. Nanodots can be engineered out of any semiconductor material. Nanodots are generally made from Group II-VI (e.g., MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe) and Group III-V (e.g., GaAs, InGaAs, InP, and InAs) semiconductor compounds that are capable of emitting electromagnetic radiation upon excitation. U.S. Pat. Nos. 6,306,736; 5,505,928; 5,262,357; and 5,990,479, which are incorporated herein by reference in their entirety, provide a description of various semiconductor nanodots and methods for forming such nanodots. Further, as described briefly above, other nanocomponents may be used as taggants and may be formed of similar material compositions. For example, CdTe nanowire can be engineered to absorb in the visible region anywhere from 500 to 650 nanometers. This specific formulation is described in the article entitled, "Spontaneous Organization of Single CdTe Nanoparticles into Luminescent Nanowires;" by Tang et al., Science, Vol. 297,12 Jul. 2002, which is incorporated by reference herein in its entirety.

The signal-to-noise engineering parameter determines the most efficient system for the detecting nanodots. As discussed above, according to the embodiments of the present invention, the nanodots can be engineered so as to emit at a different frequency than the atmosphere and the environment wherein the nanodots may be detected. For example, in normal atmospheric conditions, oxygen, carbon dioxide and water, each having large absorption bands, can be accounted for when engineering the nanodots. To optimize the signal-to-noise ratio, the nanodots are engineered to minimize the effects of these background conditions. Through engineering, rather then trying to increase the signal by just adding larger and larger quantities of the taggant as with fluorescent dyes or rare earth taggants, the current invention allows the user to move the frequency at which the taggant emits or absorbs, to a region that has minimal background noise.

In a particular embodiment of the present invention, the system and method are used to conduct bomb damage assessment ("BDA"). The release of a nanodot taggant into the environment is monitored by the stand-off detectors. By tracking and analyzing the time that it takes for the nanodot taggant to be released into the environment after detonation, taking into account environmental factors such as wind and the quantity of taggant being detected, information about the depth of the detonation and damage assessment of the interior structure can be achieved. This can be done without the need to subject humans to potentially dangerous bomb residue or structurally unsound buildings, etc.

The nanodots described herein may be encapsulated due to their small size, i.e., on the order of a couple of angstroms. The incorporation or encapsulation may be within a polymer, e.g., a polymer matrix such as polystyrene. The encapsulated nanodot taggants are on the order of 1 up to 10 microns. This size is significant due to the fact that taggants of this size will have the characteristics of a gaseous medium and behave as a gas when released into the air. The significance of this is the ability to track and monitor the movement of the taggants in order to monitor the parallel movement of, for example, biological contaminants that may be released into the atmosphere. As part of, for example, a BDA, it is important to be able to track the inadvertent release of BW agents that are harmful to humans, such as those with particle sizes less than 20 microns in diameter. Consequently, adding nanodot taggants to a reactive material, allows for modeling and tracking of the reaction plume post-reaction so as to predict where an inadvertent release of a BWA is going to migrate. From these models, it is possible to determine how the BW A is going to move, e.g., migrate towards a populated area, and take appropriate action if necessary. Similarly, the size of the nanodot taggants and the ability to encapsulate the taggants and form particles of different sizes according to the present invention, facilitates modeling and determinations of fluids other than gas or air. For example, nanodot taggants may be used to track pollutants and determine whether or not emissions criteria are being met or violated by various industries. Nanodots may be engineered in a range of sizes from 1 nm to 1 µm.

The stand-off detectors may be located on the order of 10 kilometers from the nanodot taggants and still be capable of detecting an emitted frequency. The transmitter or transmitter portion of the stand-off detector may be a laser, particle beam, high intensity light or the like. Due to the broad absorption range of the nanodots, the transmitter options are unlimited. Further, there is no requirement that the detector and transmitter be in the same location with respect to the nanodot taggants as they serve separate functions. Also, while the detectors are referred to throughout as stand-off detectors, this term is not meant to the limiting. In certain embodiments described herein, the detectors and the transmitters can be within close proximity to the target object. Existing detectors include, for example: Fourier transform infrared ("FTIR") detectors; photodiodes; chemical reaction detectors, i.e., light-sensitive chemicals and films, chemical and biological fluorescence, fluorescent organisms, light detecting molecules (e.g., rhodopsin, phytochromes, cryptochromes, flavoproteis, porphirins, and melanopsin), and light detecting organisms; detectors based upon the photoelectric effect, i.e., photomultiplier tubes, semiconductor detectors, e.g., light sensitive resistors such as cadmium sulphide detectors, photodiodes, and GaAs, Si, Ge, and InGaAs detectors, charge coupled devices and (CCDs) and focal plane arrays (FPAs); ancillary equipment and devices to tailor the light spectrum, such as filters, slits, gratings, and prisms; and instruments incorporating assemblies, devices, and ancillary equipment, such as spectrometers (e.g., Raman, IR, UV, X-ray, gamma ray), interferometers (e.g., Fourier Transform, Fabry-Perot), imaging instruments cameras, video cameras, and computer assisted scanners such as those used for medical imaging, microscopes and telescopes. Further, in an alternative embodiment, the taggants can also be collected on a filter paper-like device or similar type device, and then analyzed by standard spectroscopy in a non-stand-off detector configuration. One skilled in the art recognizes the numerous detectors and transmitters that are suitable for use with the present invention.

Available stand-off detectors have detection capabilities in excess of several kilometers and can be mounted in planes and remotely piloted vehicles or other aerial platforms. They can also be stand-alone, ground-based sensors in permanent and fixed structures or even on vehicles. Other exemplary detectors include digital cameras that are capable of detecting a taggant with a pass filter. The ability to engineer the emission and/or absorbance characteristics of the nanodot taggants allows for reduced sensitivity requirements for the detector. As such, even the most basic digital camera can detect the nanodot taggants from more than a kilometer distance.

The amount of nanodot taggant that is necessary in order to surpass the detection threshold of the stand-off detectors is minimal. Current detector technology offers the ability to detect less than a gram of nanodot taggant material, i.e., milligram amounts, from several kilometers up to and even beyond 10 kilometers distance away. The nanodot taggant may be detected at parts-per-billion (ppb) quantities.

In a second embodiment of the present invention the nanodot taggants are used to optically mark target objects, e.g., tanks, for identification. A military application of this technology is referred to as "interrogation, friend or foe" or IFF. Using nanodot taggants as the identifier or transponder of the target object, a transmitter/detector configuration may be used to optically induce emission and/or absorbance of signature spectral frequencies by the nanodots. The detection of these signature spectral frequencies identifies the target object as a friend. The optical inducement by the transmitter/detector configuration is referred to as interrogation. The current invention allows us to take this embodiment even a step further, wherein the nanodot taggant system could be used to identify a specific target object based on its emitted signature spectral frequency. By specifically engineering the spectral signature of the nanodot taggant, the spectral signature may be so difficult to mimic that the spectral signatures are in essence coded. This reduces the risk that the target object may be identified or otherwise compromised by a hostile force.

Further still, the spectral signatures of the optical markers, i.e., the nanodots, may be changed at predetermined or random intervals in order to act as a safeguard against identification or mimicking by hostile forces. For example, the target object may be marked using a changeable mechanical panel. Each panel contains a different nanodot configuration, i.e., having different spectral signatures. Consequently, at either predetermined or random time intervals, the panels can be mechanically switched to add an extra level of security to the identification of the target object. The transmitter/detector configuration, i.e., the interrogator, is similarly controlled in order to vary the transmitted inducement signal in accordance with the changing panels so as to detect the emitted spectral signature.

Alternatively, the optical marker could be in the form of a changeable liquid panel, wherein the panel is drained of a liquid containing a first nanodot taggant and re-filled with a liquid containing a second nanodot taggant, and so on. Finally, a portion of the target object may simply be painted with a nanodot taggant material. The marking capacity of the nanodot taggants may also be used in a tracer capacity. The nanodot taggants may be utilized as additives to any number of materials including explosives, chemicals, plastics, fuels, or other materials, such that at some later time, through optical identification, one can identify and track that material, where it originated from and where it is presently located.

In yet a further embodiment of the present invention, the nanodots may be engineered and mixed to duplicate the spectral signature of another substance. For example, there presently exists a need in the art for compounds that simulate or mimic the spectral signatures of agents of chemical and biological warfare (CBW). Due to their severe toxicity, these 'live' CBW agents must be handled with extreme caution and can not be dispersed into the environment. It is therefore very difficult to validate diagnostic instruments, e.g., detectors, for studying and identifying CBW agents. As described above, nanodots may be engineered so as to have a particular absorbance and/or emission spectral characteristic. Further, since these nanodots are, for the most part, chemically inert, nanodots with varying absorbance and/or emission spectral characteristics may be mixed. These mixtures can mimic the spectral signature of CBW agents and the nanodots can be used to simulate these hazardous compounds. Similarly, this compound simulation is not limited to CBW agents, but can be used to mimic any compound that has a spectral signature in the UV, visible, or infra-red spectrums. Examples of these compounds include, but are not limited to, controlled substances such as compounds of the opioid family and chemicals, which are invaluable due to their production and/or purification costs. Such simulation, as described for CBW agents, can be used to determine 'reference' and 'calibration' standards for optical instruments, such as UV-Visible spectrophotometers and the like. One skilled in the art recognizes the additional simulation embodiments that fall within the scope of the embodiments described herein.

In certain of the embodiments described herein, the nanodot taggants may be added to the reaction material or the target object in a number of ways, depending on the intended application of the nanodot taggant. For example, in the explosive taggant application, adding a nanodot taggant to a reactive mixture can be achieved by directly adding the taggant to the mixture. Alternatively, since the reactive mixture is almost always housed in a missile or other type of compartmental device, the nanodot taggant may be added to a fuse well or to the casing of the missile or device. In yet an alternative embodiment, nanodot taggants may be added to a room, cave, or other enclosed space, wherein activity may be monitored by tracking the movement of the nanodot taggant within the room, cave, entrance, or other space. The disruptions in the pattern of the nanodot taggants throughout the room indicate types and amount of disruptions through nanodot taggant displacement.

Specifically engineered nanodot taggants as described herein may also be used to covertly mark, identify, and or authenticate other objects that are often forged or stolen. The other objects include munitions, aircraft, auto, or other parts; stamps; negotiable financial instruments (e.g., currency, checks, stamps, vouchers, stock certificates, bonds, script, food stamps, etc.); identification and travel documents, passports, ID cards, visas, health cards, etc.); identification labels such as those utilized in the apparel industry; and packaging or seals on items such as CDs, videotapes or software, etc. The nanodot taggants described herein are, for the most part, chemically inert and the quantities necessary for detection are so minute that inclusion of the nanodot taggants within the objects or during formation of the objects, does not result in adverse impacts on the efficiency or safety of the objects. Furthermore, the nanodots can be covalently attached to a wide variety of materials through surface chemistry methods. For example, the nanodots can be bound to polymers such as nylon or rayon and subsequently incorporated into other manufactured products such as clothing or plastics.

Similarly, nanodots may for the basis for a taggant that may be used to identify and authenticate perfumes, cosmetics, pharmaceuticals, as well as food, beverages, and luxury items such as tobacco. The extremely small size of the nanodots allows for the ability to encapsulate the nanodots, if necessary, so as to be safe for human consumption. Further, since the nanodots can be engineered for specific absorption and/or emission frequencies for ready detection, the amount of taggant added to products can be minimized. As described above, taggants formed of nanodots, as set forth herein, can be detected from significant distances without the need for a direct line-of-sight configuration. Consequently, the detection and authentication of products can be performed from significant distances in real-time without the need for invasive testing. As such, the system and methods described herein facilitate fast and efficient product authentication.

The embodiments described herein are not intended to be limiting. One skilled in the art recognizes those alternative materials, methods, and uses that fall within the spirit and scope of the disclosed invention.

The invention claimed is:

1. A process for identifying a target object comprising:

placing a first panel containing a first nanocomponent taggant in a first liquid to a target object, wherein the first nanocomponent taggant emits at least a first predefined spectral frequency in response to interrogation;

transmitting a first radiation at the target object in order to induce emission of the at least a first predefined spectral frequency from the first nanocomponent taggant in the first panel;

detecting the at least a first predefined spectral frequency emitted from the target object in order to identify the target object; and mechanically changing a spectral signature of the target object by replacing the first liquid containing the first nanocomponent taggant with a second liquid containing a second nanocomponent taggant that emits a second predefined spectral frequency in response to interrogation by second radiation.

2. The process according to claim 1, wherein the first liquid is replaced at a predetermined interval.

3. The process according to claim 1, wherein the first liquid is replaced at a random interval.

\* \* \* \* \*